United States Patent
Koch et al.

(10) Patent No.: US 10,478,090 B2
(45) Date of Patent: Nov. 19, 2019

(54) SPECTRAL BIN UN-ALIASING FOR REDUCED FIELD-OF-VIEW MAGNETIC RESONANCE IMAGING NEAR METAL IMPLANTS

(71) Applicant: Medical College of Wisconsin, Milwaukee, WI (US)

(72) Inventors: Kevin Matthew Koch, Wauwatosa, WI (US); Andrew Scott Nencka, Milwaukee, WI (US)

(73) Assignee: Medical College of Wisconsin, Milwaukee, WI (US)

( * ) Notice: Subject to any disclaimer, the term of this patent is extended or adjusted under 35 U.S.C. 154(b) by 0 days.

(21) Appl. No.: 16/094,525

(22) PCT Filed: Apr. 24, 2017

(86) PCT No.: PCT/US2017/029155
§ 371 (c)(1),
(2) Date: Oct. 18, 2018

(87) PCT Pub. No.: WO2017/185090
PCT Pub. Date: Oct. 26, 2017

(65) Prior Publication Data
US 2019/0150781 A1    May 23, 2019

Related U.S. Application Data

(60) Provisional application No. 62/326,453, filed on Apr. 22, 2016.

(51) Int. Cl.
*A61B 5/055* (2006.01)
*G01R 33/561* (2006.01)
*G01R 33/48* (2006.01)
*G01R 33/565* (2006.01)

(52) U.S. Cl.
CPC .......... *A61B 5/055* (2013.01); *G01R 33/4822* (2013.01); *G01R 33/5611* (2013.01); *G01R 33/56536* (2013.01)

(58) Field of Classification Search
CPC .......................... A61B 5/055; G01R 33/5611
USPC ....................................................... 324/309
See application file for complete search history.

(56) References Cited

U.S. PATENT DOCUMENTS 9,989,613 B2 *  6/2018  Wiens .............. G01R 33/56536
2006/0119623 A1   6/2006  Quigley
(Continued)

OTHER PUBLICATIONS

International Search Report and Written Opinion for International Application No. PCT/US2017/029155, dated Jun. 30, 2017, 23 pages.
(Continued)

*Primary Examiner* — Reena Aurora
(74) *Attorney, Agent, or Firm* — Foley & Lardner LLP

(57) ABSTRACT

A magnetic resonance imaging (MRI) system can include a magnetic resonance imaging (MRI) scanner, having a plurality of radio frequency (RF) receivers, and a processor. The MRI scanner can perform a full field of view (fFOV) scan on an anatomy area including an implant to acquire first multi-spectral MRI data associated with a plurality of frequency bins. The processor can generate, for each pair of a single RF receiver and a single frequency bin, a respective spectral sensitivity map using at least a portion of the fFOV multi-spectral MRI data. The MRI scanner can perform a reduced FOV (rFOV) scan to acquire second multi-spectral MRI data associated with the plurality of frequency bins. The processor can reconstruct one or more MRI images according to the rFOV using the rFOV multi-spectral MRI data and the spectral sensitivity maps.

20 Claims, 6 Drawing Sheets

(56) References Cited

U.S. PATENT DOCUMENTS

| | | |
|---|---|---|
| 2010/0308827 A1 | 12/2010 | Koch et al. |
| 2011/0103670 A1* | 5/2011 | Koch ............ G01R 33/243 382/131 |
| 2011/0241676 A1 | 10/2011 | Busse et al. |
| 2013/0265046 A1 | 10/2013 | Koch |
| 2014/0043023 A1 | 2/2014 | Reeder et al. |
| 2014/0266191 A1 | 9/2014 | Sveinsson et al. |
| 2014/0376794 A1 | 12/2014 | Dumoulin et al. |
| 2015/0145514 A1 | 5/2015 | Sharma et al. |
| 2018/0292496 A1* | 10/2018 | Kaushik ............ G01R 33/5608 |

OTHER PUBLICATIONS

Koch et al., Magnetic resonance imaging near metal implants, Journal of Magnetic Resonance Imaging, dated Sep. 29, 2010, 42 pages.

Griswold et al., Generalized Autocalibrating Partially Parallel Acquisitions (GRAPPA), Magnetic Resonance in Medicine 47, 2002, 9 pages.

Hargreaves et al., Fast 2D Imaging for Distortion Correction Near Metal Implants, Proc. Intl. Soc. Mag. Reson. Med. 22, 2014, 1 page.

Koch et al., A Multispectral Three-Dimensional Acquisition Technique for Imaging Near Metal Implants, Magnetic Resonance in Medicine 61, 2009, 10 pages.

Koch et al., Imaging Near Metal with a MAVRIC-SEMAC Hybrid, Magnetic Resonance in Medicine 65, 2011, 12 pages.

Lu et al., SEMAC: Slice Encoding for Metal Artifact Correction in MRI, Magnetic Resonance in Medicine 62, 2009, 11 pages.

Pruessmann et al., SENSE: Sensitivity Encoding for Fast MRI, Magnetic Resonance in Medicine 42, 1999, 11 pages.

Smith et al., Accelerating Sequences in the Presence of Metal by Exploiting the Spatial Distribution of Off-Resonance, Magnetic Resonance in Medicine 72, 2014, 10 pages.

\* cited by examiner

SPECTRAL BIN UN-ALIASING FOR REDUCED FIELD-OF-VIEW MAGNETIC RESONANCE IMAGING NEAR METAL IMPLANTS

RELATED APPLICATION

The present application claims priority to U.S. Provisional Application No. 62/326,453, entitled "SPECTRAL BIN UN-ALIASING FOR REDUCED FIELD-OF-VIEW MAGNETIC RESONANCE IMAGING NEAR METAL IMPLANTS" and filed on Apr. 22, 2016, which is incorporated herein by reference in its entirety for all purposes.

BACKGROUND

Metallic device implantation is widely used in the medical field to manage a variety of acute traumatic and chronic arthritic medical conditions, such as arthroplasty for osteoarthritis, fixation for fracture repair and joint replacement following neoplasm resection. Assessing bone and soft tissue in the vicinity of implanted orthopedic devices is vital for identification of complications related to the implants themselves, such as adverse local tissue reactions often found near total hip replacements. In addition, assessment of regions near implanted devices allows for pain evaluation following instrumentation. Such assessment may reflect a diverse set of conditions, including infection, osteonecrosis and recurrent tumor.

Increasing rates of primary and revised joint replacements together with the medical complications associated with implanted orthopedic devices call for accurate and reliable diagnostic imaging in the presence of orthopedic implants. It is projected that by 2030 clinicians will perform nearly 500,000 hip replacements and 3.5 million knee replacements in the United States alone. These projections also predict that nearly 100,000 hip revisions and more than 250,000 knee revision procedures will occur annually in the United States by 2030.

Magnetic Resonance Imaging (MRI) soft-tissue contrast can add substantial diagnostic value when assessing the tissue envelope around metallic implants. For example, the United States Food and Drug Association (FDA) issued a recommendation for using MRI in imaging assessments of recently recalled total hip replacements. However, magnetic susceptibility artifacts generated by implants have historically limited MRI's practical clinical application in assessments of instrumented joints. Several years ago, Three-Dimensional Multi—Spectral Imaging (3D-MSI) technology was developed by the MRI research community including inventors of this disclosure—to reduce susceptibility artifacts due to implanted devices.

BRIEF DESCRIPTION OF THE DRAWINGS

Embodiments of the inventive concepts disclosed herein will become more fully understood from the following detailed description, taken in conjunction with the accompanying drawings, wherein like reference numerals refer to like elements, in which.

Figure 1:
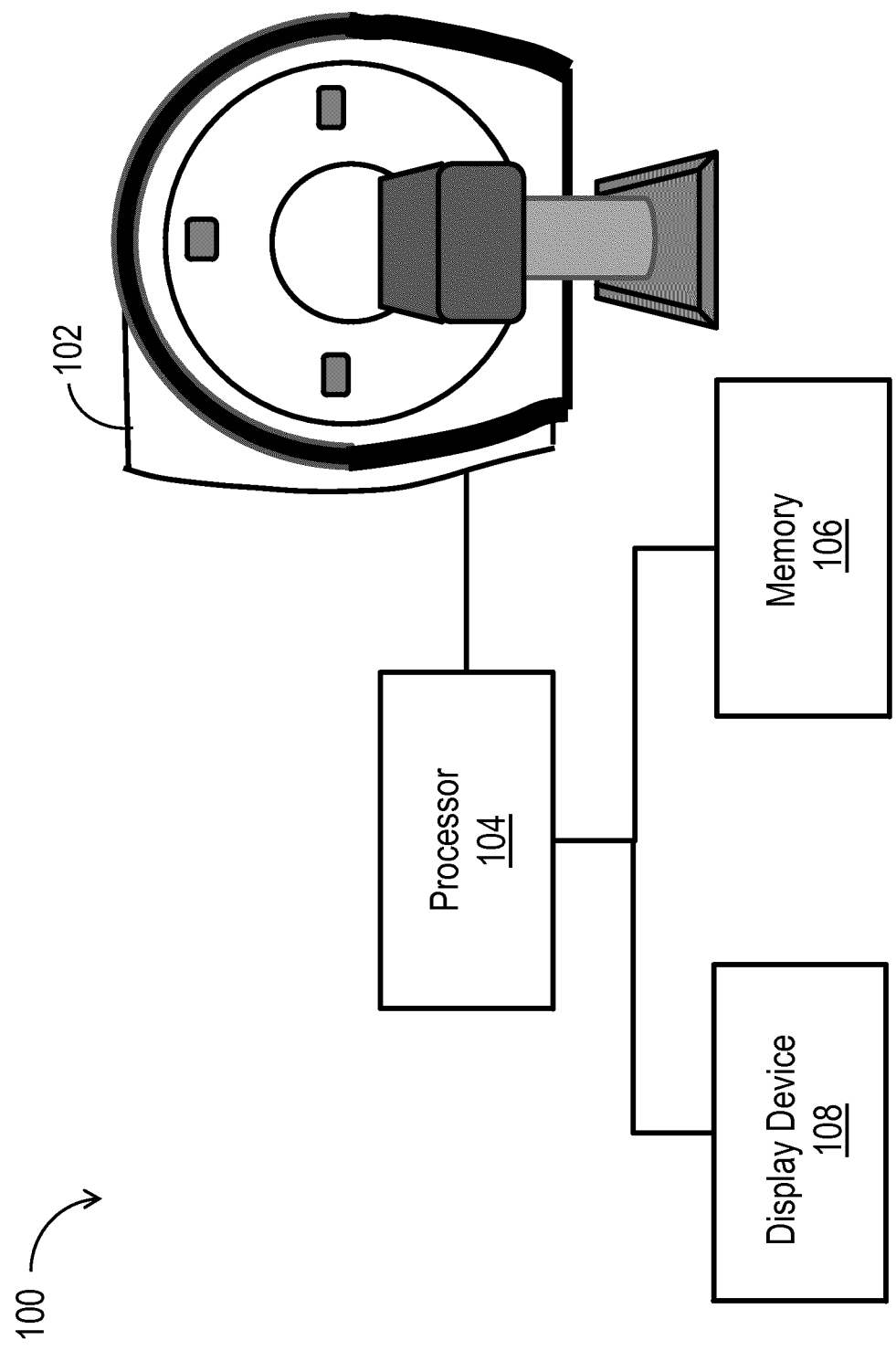
FIG. 1 is a block diagram illustrating a magnetic resonance imaging (MRI) system, according to inventive concepts of this disclosure.

The details of various embodiments of the methods and systems are set forth in the accompanying drawings and the description below.

SUMMARY

According to at least one aspect, a magnetic resonance imaging (MRI) system can include a magnetic resonance imaging (MRI) scanner, at least one processor, and a memory. The MRI scanner can include a plurality of radio frequency (RF) receivers for imaging objects of interest. The memory can include computer code instructions stored thereon. The computer code instructions, when executed by the at least one processor, can cause the at least one processor to cause the MRI scanner to perform a first scan, on an anatomy region including an implant, according to a first field of view to acquire first multi-spectral MRI data associated with a plurality of frequency bins. The at least one processor can generate, for each pair of a single RF receiver and a single frequency bin, a respective spectral sensitivity map using at least a portion of the first multi-spectral MRI data. The at least one processor can cause the MRI scanner to perform a second scan according to a second field of view to acquire second multi-spectral MRI data associated with the plurality of frequency bins. The second field of view can be smaller than the first field of view. The at least one processor can reconstruct one or more MRI images according to the second field of view using the second multi-spectral MRI data and the spectral sensitivity maps.

The first field of view can be a full field of view. The first field of view can be an integer multiple of the second field of view. The first field of view can be a non-integer multiple of the second field of view. Performing the second scan can include selecting a "no phase-wrap" option or a "fold-over suppression" option when acquiring second multi-spectral MRI data. The selection of the "no phase-wrap" option or the "fold-over suppression" option can cause the processor to perform unaliasing on the second multi-spectral MRI data using the sensitivity maps.

Reconstructing the one or more MRI images according to the second field of view can include performing unaliasing correction to the to the second multi-spectral MRI data in image-space (x, y, z). Reconstructing the one or more MRI images according to the second field of view can include performing unaliasing correction to the second multi-spectral MRI data in k-space (kx, ky, kz). Reconstructing the one or more MRI images according to the second field of view can include performing unaliasing correction to the second multi-spectral MRI data in a hybrid space. The hybrid space can include one or more dimensions in image-space and one or more dimensions in k-space. Reconstructing the one or more MRI images according to the second field of view can include applying autocalibrated parallel imaging to the second multi-spectral MRI data prior to performing unaliasing of the second multi-spectral MRI data.

According to at least one aspect, a magnetic resonance imaging (MRI) method can include a MRI scanner having a plurality of radio frequency (RF) receivers performing a first scan according to a first field of view to acquire first multi-spectral MRI data associated with a plurality of frequency bins and corresponding to an anatomy area including an implant. The method can include a processor generating, for each pair of a single RF receiver and a single frequency bin, a respective spectral sensitivity map using at least a portion of the first multi-spectral MRI data. The method can include the MRI scanner performing a second scan according to a second field of view to acquire second multi-spectral MRI data associated with the plurality of frequency bins and corresponding to the anatomy area including an implant. The second field of view can be smaller than the first field of view. The method can include the processor reconstructing one or more MRI images according to the second field of view using the second multi-spectral MRI data and the spectral sensitivity maps.

The first field of view can be a full field of view. The first field of view can be an integer multiple of the second field of view. The first field of view can be a non-integer multiple of the second field of view. Performing the second scan can include selecting a "no phase-wrap" option or a "fold-over suppression" option when acquiring second multi-spectral MRI data. The selection of the "no phase-wrap" option or the "fold-over suppression" option can cause the processor to perform unaliasing on the second multi-spectral MRI data using the sensitivity maps.

Reconstructing the one or more MRI images according to the second field of view can include performing unaliasing correction to the to the second multi-spectral MRI data in image-space (x, y, z). Reconstructing the one or more MRI images according to the second field of view can include performing unaliasing correction to the second multi-spectral MRI data in k-space (kx, ky, kz). Reconstructing the one or more MRI images according to the second field of view can include performing unaliasing correction to the second multi-spectral MRI data in a hybrid space. The hybrid space can include one or more dimensions in image-space and one or more dimensions in k-space. Reconstructing the one or more MRI images according to the second field of view can include applying autocalibrated parallel imaging to the second multi-spectral MRI data prior to performing unaliasing of the second multi-spectral MRI data.

According to at least one aspect, a non-transitory computer-readable medium can include computer executable instructions stored thereon. The computer executable instructions, when executed by a processor, can cause the processor to cause an MRI scanner, having a plurality of radio frequency (RF) receivers, to a perform a first scan according to a first field of view to acquire first multi-spectral MRI data associated with a plurality of frequency bins and corresponding to an anatomy area including an implant. The processor can generate, for each pair of a single RF receiver and a single frequency bin, a respective spectral sensitivity map using at least a portion of the first multi-spectral MRI data. The processor can cause the MRI scanner to a perform a second scan according to a second field of view to acquire second multi-spectral MRI data associated with the plurality of frequency bins and corresponding to the anatomy area including an implant. The second field of view can be smaller than the first field of view. The processor can reconstruct one or more MRI images according to the second field of view using the second multi-spectral MRI data and the spectral sensitivity map.

The first field of view can be a full field of view. The first field of view can be an integer multiple of the second field of view. The first field of view can be a non-integer multiple of the second field of view. Performing the second scan can include selecting a "no phase-wrap" option or a "fold-over suppression" option when acquiring second multi-spectral MRI data. The selection of the "no phase-wrap" option or the "fold-over suppression" option can cause the processor to perform unaliasing on the second multi-spectral MRI data using the sensitivity maps.

Reconstructing the one or more MRI images according to the second field of view can include performing unaliasing correction to the to the second multi-spectral MRI data in image-space (x, y, z). Reconstructing the one or more MRI images according to the second field of view can include performing unaliasing correction to the second multi-spectral MRI data in k-space (kx, ky, kz). Reconstructing the one or more MRI images according to the second field of view can include performing unaliasing correction to the second multi-spectral MRI data in a hybrid space. The hybrid space can include one or more dimensions in image-space and one or more dimensions in k-space. Reconstructing the one or more MRI images according to the second field of view can include applying autocalibrated parallel imaging to the second multi-spectral MRI data prior to performing unaliasing of the second multi-spectral MRI data.

DETAILED DESCRIPTION

Advanced methods for imaging around metallic implants, such as multi-spectral imaging (MSI) methods, yield most benefit in the neighborhood around the implant. In particular, it is often desirable, in cases where multi-spectral imaging is employed, to image a reduced field of view of a body region where an implant is located. Reduced field of view imaging of such body region can allow for generating higher resolution images focused on the areas in the vicinity of the implant, which are more relevant than distant areas for the diagnosis of medical conditions associated with implants. Also, reduced field imaging can lead to reduced MRI scan time. Long MRI scan time can make patients uncomfortable and more likely to move during the scanning process. Patient movement, in such cases, can introduce serious artifacts that may undermine the diagnostic value of the generated images.

However, the extent of the anatomy in the body region of the implant often calls for large field of view acquisitions. For example, reduced field of view imaging can result in imaging artifacts resulting from aliasing. Aliasing can occur whenever the area of anatomy being imaged extends beyond the field of view. Areas extending beyond the field of view boundaries are "aliased" back (wrapped around) into the reconstructed image to appear at artefactual locations. For instance, portions of an object outside of the desired field of view can be mapped to an incorrect location inside the field of view. Therefore, while MSI techniques can greatly minimize imaging distortions caused by metal implants, novel and inventive concepts to allow reduced field of view MR imaging near metallic implants can further improve the performance and diagnostic value of multi-spectral MR imaging.

According to inventive concepts of this disclosure, multi-spectral MR imaging methods and systems that combine spatially varying coil sensitivity profiles with spatially varying resonance frequency bins can significantly reduce the imaged field of view without degrading the quality and the diagnostic value of the produced MR images. In particular, multi-spectral MR imaging methods and systems employing rapid spatially varying resonance frequency bins and reduced field of view (rFOV) acquisitions can produce MR images free from aliasing artifact regions in the neighborhood of implants. These multi-spectral MR imaging methods and systems include using low-resolution pre-scan acquisition (also referred to as calibration acquisition or reference scan calibration) data to eliminate (or mitigate) aliasing artifacts in MR imaging data obtained in a subsequent rFOV acquisition. While, rFOV MRI data associated with spectral bins usually includes aliasing artifacts, methods and systems described herein can employ the low-resolution MRI data acquired during a pre-scan to "un-alias" the rFOV MRI data and produce relatively (e.g., compared to other MR imaging techniques know in the art) clean rFOV images around metal implants.

FIG. 1 is a block diagram illustrating a magnetic resonance imaging (MRI) system 100, according to inventive concepts of this disclosure. In brief overview, the MRI system 100 can include a MRI scanner 102, a processor 104, a memory 106, and a display device 108. The processor 104 can be communicatively coupled to the MRI scanner 102, the memory 106 and the display device 108.

The MRI scanner 102 can include a plurality of radio frequency (RF) receiver channels or coils (not shown in FIG. 1). For example, the MRI scanner 102 can include a plurality of phased-array coils that allow parallel imaging. The MRI scanner 102 can be configured to support multi-spectral imaging data acquisition. The MRI scanner 102 may acquire multi-spectral imaging data according to one or more pre-determined acquisition patterns. The MRI scanner 102 can provide acquired imaging data to the processor 104 directly or indirectly via the memory 106.

The imaging system 100 can include one or more processors 104. The one or more processors 104 can include a processor integrated within the MRI scanner 102, a processor of a computing device communicatively coupled to the MRI scanner 102, or a combination thereof. The memory 106 can include a memory component of the MRI scanner 102, a memory component of a computing device communicatively coupled to the MRI scanner 102, or a combination thereof. The memory 106 can include computer executable instructions, which when executed by the one or more processors 104, can cause the one or more processors 104 to perform reduced field of view (rFOV) multi-spectral imaging (MSI) methods described herein, such as the method described below with regard to FIG. 2, or steps thereof.

The display device 108 can include a cathode ray tube (CRT) display, a light emitting diode (LED) display, an organic light emitting diode (OLED) display, a plasma display panel (PDP), a liquid crystal display (LCD), or other display known to a person of ordinary skill in the art. The display device 108 may be a stand-alone device or a display of a computing device (e.g., a desktop, laptop, or tablet) communicatively coupled to the MRI scanner 102. The display device can include a touch screen. The display device 108 can receive image data from the processor 104 or the memory 106 and display the received image data. For example, upon reconstructing MRI images based on data acquired by the MRI scanner 102, the processor 104 can provide the reconstructed images for display on the display device 108.

Figure 2:
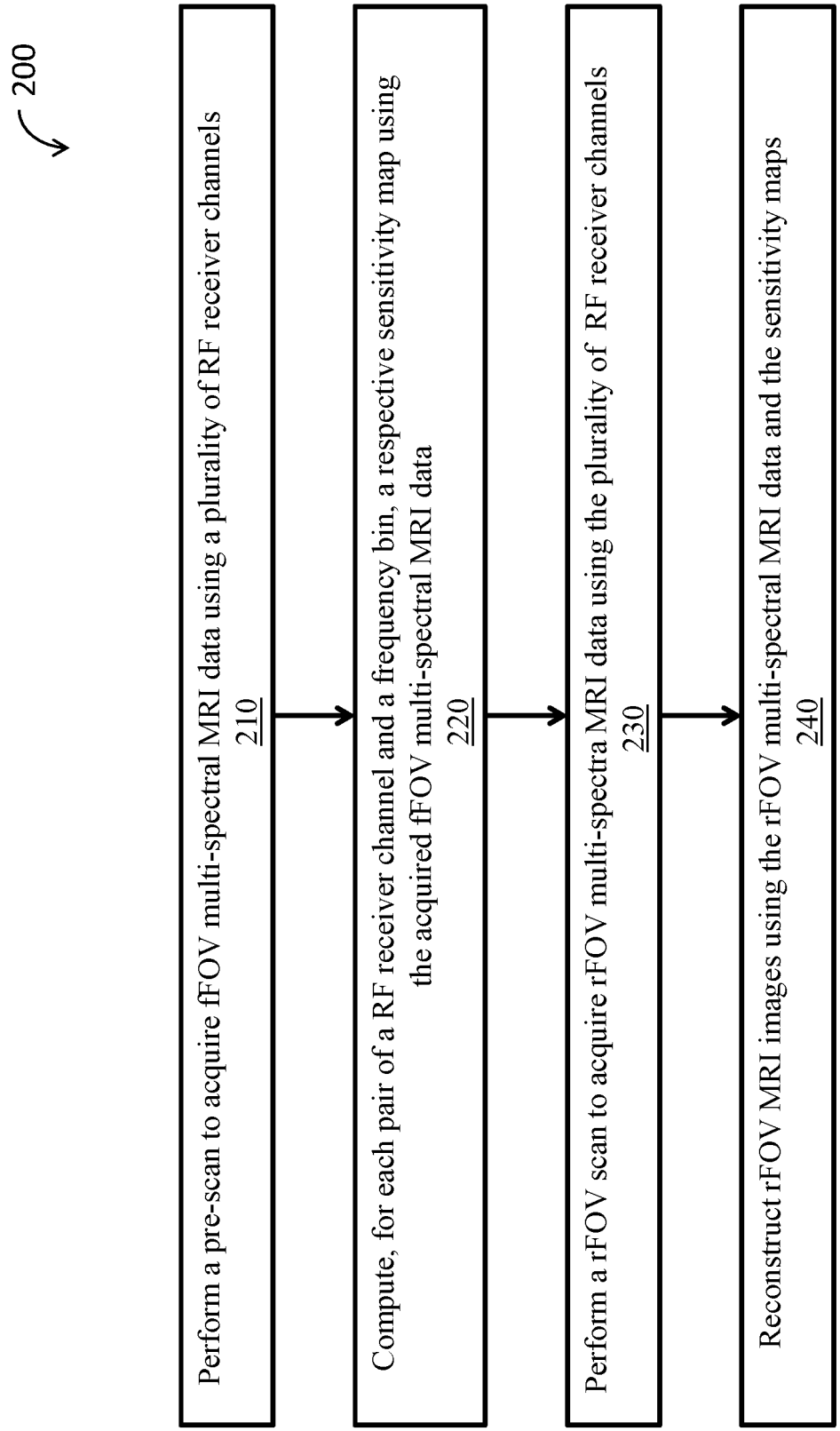
FIG. 2 is a flowchart illustrating a method of reduced field of view multi-spectral imaging (MSI), according to inventive concepts of this disclosure.

FIG. 2 is a flowchart illustrating a method 200 of reduced field of view (rFOV) multi-spectral imaging (MSI), in accordance with example embodiments of this disclosure. The method 200 can be employed for imaging near metal implants. The method 200 can include the MRI scanner 102 performing a pre-scan to acquire a first set of multi-spectral MRI data corresponding to a first field of view (FOV) (step 210), and the processor 104 generating, for each pair of a RF receiver channel and a frequency bin, a respective sensitivity map using the acquired first FOV multi-spectral MRI data (step 220). The method 200 can include the MRI scanner 102 performing a scan to acquire a second set of multi-spectral MRI data corresponding to a second FOV (step 230), and the processor 104 reconstructing un-aliased MRI images using the second set of multi-spectral MRI data corresponding to the second FOV and the sensitivity maps (step 240).

The method 200 can include the MRI scanner 102 performing a pre-scan to acquire the first set of multi-spectral MRI data (step 210). The MRI scanner 102 can scan an object of interest (such as a body region of a patient including an implant) according to a plurality of frequency offset bins. The pre-scan (or calibration) acquisition can be associated with a first field FOV. In general, the first FOV can be larger than the second FOV. For instance, the first FOV can be a full field of view (fFOV). In a fFOV (also referred to as skin-to-skin view) acquisition, a region of anatomy (or an object, in general) is fully imaged and the region of anatomy does not extend beyond the FOV at least along one dimension. For example, for a patient having an implanted rod in one leg, both legs (e.g., from left skin boundary of the left leg to right skin boundary of the right leg) would be imaged by the MRI scanner. Imaging skin-to-skin leaves no portions of anatomy beyond the fFOV. In some instances, the first FOV multi-spectral MRI data (also referred to as "calibration data") can have a relatively low resolution (e.g., compared to typical resolutions used by radiology technicians to image the same object of interest). For example, while typical MRI data can have a resolution of 256×256, the calibration data can have a resolution of 128×32, 128×64, or other resolution smaller than the resolution of typical MRI data. In some implementations, the pre-scan can last for a relatively short time period (such as about 1-2 minutes).

The MRI scanner 102 can acquire the first FOV multi-spectral MRI data sequentially. For example, the MRI scanner 102 can acquire MRI data corresponding to a first frequency bin, then acquire MRI data corresponding to a second frequency bin, and son and so forth until the MRI data for all frequency bins is acquired. For each frequency bin, the MRI scanner can acquire MRI data at a plurality of RF receiver channels. For example, the MRI scanner 102 can have M receiver channels and can acquire MRI data for N frequency bins.

The method 200 can include the processor generating, for each pair (i, j) including frequency bin i and RF receiver channel j, a respective sensitivity map using the acquired low-resolution first FOV multi-spectral MRI data (step 220). The integer i can represent a frequency bin index between 0 and N−1, and the integer j can represent a RF receiver channel index between 0 and M−1. Generating the sensitivity maps can include the processor 104 constructing one or more pre-scan (or calibration) MR images using the acquired first FOV multi-spectral MRI data.

Figure 3:
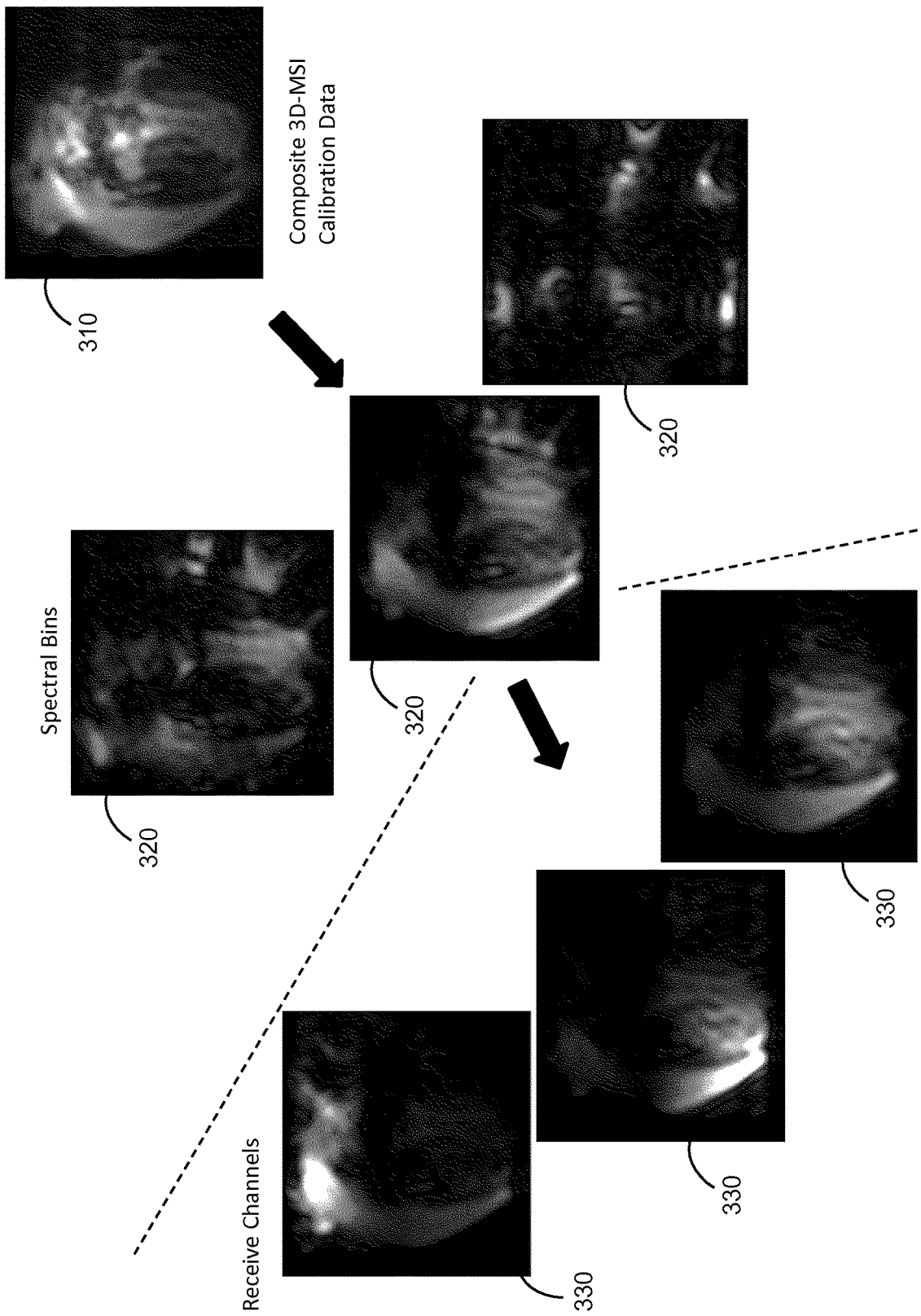
FIG. 3 shows images illustrating example sensitivity maps data, spectral bin data, and composite three-dimensional (3D) multi-spectral imaging (MSI) calibration data.

Referring to FIG. 3, images illustrating example sensitivity maps, spectral bin MM images, and a composite three-dimensional (3D) multi-spectral imaging (MSI) calibration image generated based first FOV data are shown. The processor 104 can construct a composite three dimensional (3D) MSI image 310 using, for example, acquired fFOV multi-spectral MRI data from all RF receiver channels corresponding to all frequency bins. The processor 104 can generate a plurality of frequency bin images 320. Each frequency bin image 320 corresponds to a respective frequency bin. For each frequency bin, the processor 104 can generate a respective frequency bin image 320 using, for example, MM data acquired from all RF receiver channels for that frequency bin. For each pair (i,j) including the frequency bin i and the RF receiver channel j, the processor 104 can generate a respective sensitivity map 330. The processor 104 can generate the sensitivity map 330 corresponding to the pair (i,j) using MRI data corresponding to frequency bin i acquired from RF receiver channel j. Generating the sensitivity maps 330 can include the processor 104 normalizing MRI data associated with each pair (i,j) using data associated with the composite three dimensional (3D) MSI image 310 or the frequency bin images 320. The sensitivity map corresponding to the pair (i,j) represents the sensitivity of the RF receiver j to RF signals, corresponding to frequency bin i, from various voxels of the imaged object.

Referring again to FIG. 2, the method 200 can include the MRI scanner 102 performing a scan to acquire a second set of multi-spectral MRI data corresponding to the second FOV (step 230). The second FOV can be a rFOV that is smaller than the fFOV by at least a factor of 2 in one or more dimensions (e.g., one of the dimensions in the x, y, or z directions). For example, the rFOV can be smaller than the fFOV by an integer factor of 2, 4, 8, or other integer in one or more dimensions. In some embodiments, the second FOV (or rFOV) can be smaller than the first FOV (or fFOV) by a non-integer factor in one or more dimensions (such as a factor of 1.5 or 1.75). Also, the rFOV multi-spectral MRI data can have a resolution higher than the resolution of the acquired first FOV (or fFOV) multi-spectral MRI data. For example, the resolution of the rFOV multi-spectral MRI data can be higher than the resolution of the acquired fFOV multi-spectral MRI data by an integer factor of 2, 4, or 8 (or by a non-integer factor) in one or more dimensions.

The method 200 can also include the processor 104 reconstructing un-aliased rFOV MRI images using the rFOV multi-spectral MRI data and the sensitivity maps (step 240). The processor 104 can employ parallel imaging techniques to reconstruct the un-aliased rFOV MRI images. When employing parallel imaging, the processor 104 can perform (or apply) unaliasing correction to remove (or mitigate) aliasing artifacts from the rFOV multi-spectral MRI data either (1) in the image domain (or image-space (x, y, z)), or (2) in the complex frequency domain (or k-space (kx, ky, kz)).

With regard to unaliasing correction in the image-space, the processor 104 can employ the SENSitivity Encoding (SENSE) un-aliasing method (or algorithm) to eliminate aliasing in the aliased rFOV MRI data. With regard to unaliasing correction in the k-space, the processor can employ, for example, autocalibrating parallel imaging such as the Generalized Autocalibrating Partially Parallel Acquisitions (GRAPPA) un-aliasing method (or algorithm) to eliminate aliasing in the one or more aliased rFOV MRI images.

In some embodiments, the processor 104 can also employ hybrid parallel imaging techniques to perform unaliasing correction in a hybrid space. In a hybrid space, at least one dimension of the data is image space and at least one dimension is in the k-space (e.g., the two-dimensional hybrid space (x, ky)). The processor 104 can, for example, transform the acquired (aliased) rFOV data by applying one dimensional (1D) FT in the readout direction. The processor 0104 can use the sensitivity maps to determine coefficient for synthesizing missing data in the transformed rFOV data to correct for aliasing.

In some embodiments, the processor 104 can apply autocalibrating parallel imaging (e.g., GRAPPA) on rFOV data to perform a first stage of unaliasing, and then use the fFOV data (or the sensitivity maps) to perform a second stage unaliasing on the rFOV data. This allows for parallel-image based undersampling of the rFOV acquisition, while still allowing for unaliasing of the rFOV fold-over artifacts.

The un-aliased rFOV MRI image(s) reconstructed by the processor can include a composite rFOV MRI image and/or a plurality of rFOV un-aliased images corresponding to the plurality of frequency bins. Once the un-aliased rFOV MRI image(s) are reconstructed, the processor 104 can provide such the reconstructed images to the memory 106 for storage thereon, or to the display device 108 for display thereon.

Existing metal artifact reduction technologies are incompatible with commonly utilized "no-phase-wrap", "fold-over suppression", or "frequency oversampling" technologies that allow for targeted fields-of-view around joints or organs of interest. Embodiments of the systems and methods described herein can effectively enable such "phase-wrap" suppression technology to metal artifact reduction sequences. As a result, images of commonly studied joints like total hip replacements can be acquired at higher resolution. The systems and methods described herein also improve diagnostic Mill pertaining to a wide variety of acute traumatic and chronic medical conditions in which in-dwelling metallic implants are a factor. Certain portions of the systems and methods described herein can be implemented as software, hardware, or a combination thereof. These systems and methods can be implemented with a variety of MR scanners or by adapting certain MR scanners (such as MR scanners by GE Healthcare, Siemens, and Phillips) for producing undistorted, reduced field-of-view images around metallic implants.

In some embodiments, the MRI scanner 102 can be configured to support a "no-phase-wrap" mode (or option), a "fold-over suppression" mode (or option), or a "frequency oversampling" mode (or option). Such a mode can be selected via button or a display of the MRI scanner 102 or through a user interface (UI) provided by the processor 104 (e.g. the UI can be displayed on the display device 108). Selection of such mode (or option) when performing an imaging task can cause the processor 104 and/or the MRI scanner 102 to perform the imaging task according to the method(s) described with regard to FIG. 2. In particular, selection of such mode (or option) can cause the processor 104 to perform unaliasing correction on the acquired rFOV data using the first FOV (or fFOV) data or the sensitivity maps.

Figure 4:
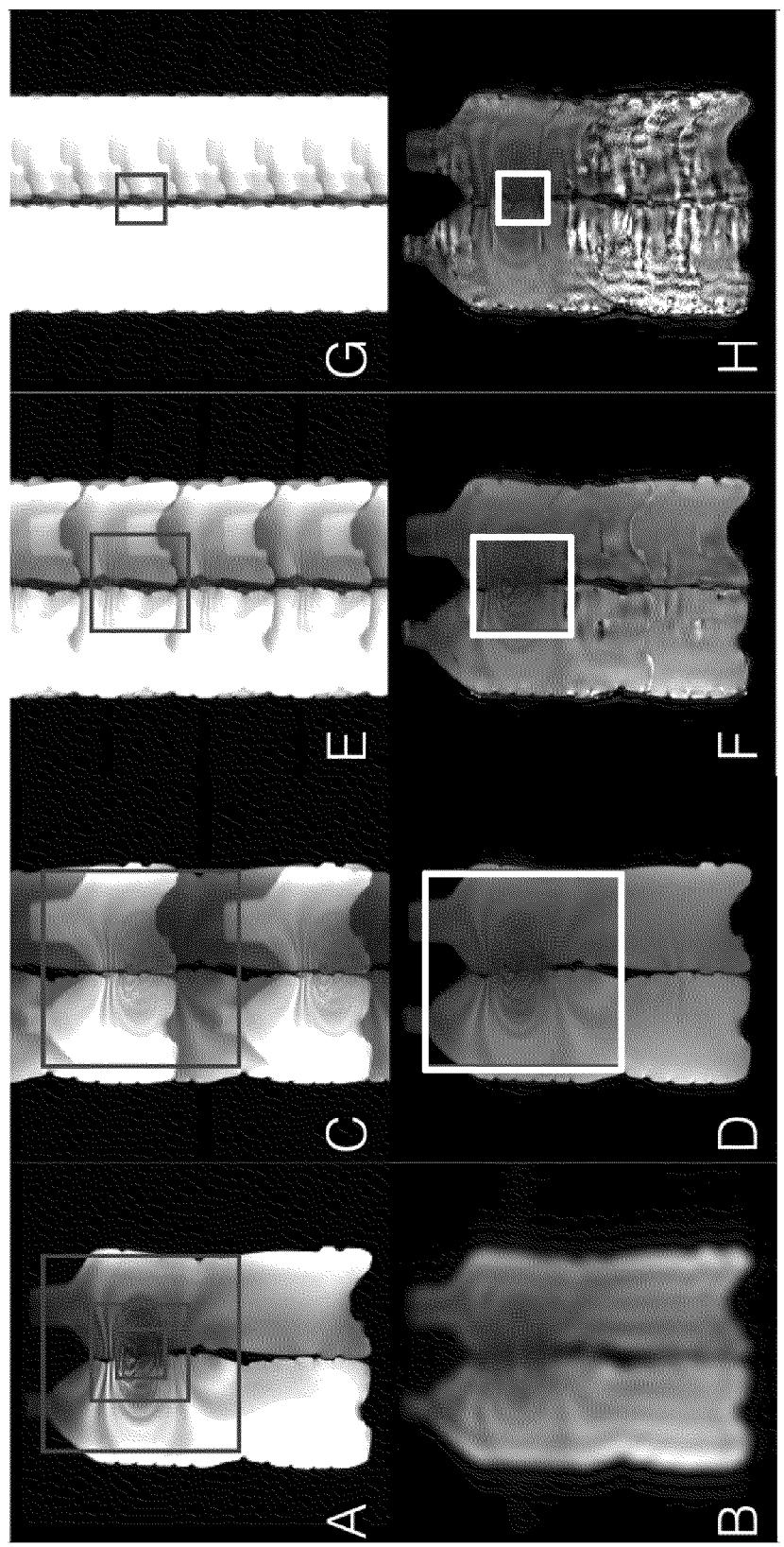
FIG. 4 shows experimental results based on two dimensional MSI acquisitions using a water phantom with an included Co/Cr orthopedic device.

FIG. 4 shows experimental results based on two dimensional MSI acquisition using a water phantom with an included Co/Cr orthopedic device (imaged using GE Discovery MR750 3T). The imaging parameters for the phantom include 256 matrix, TE 7.1 ms, TR 5000 ms, 16 frequency bins, 1 kHz bin width, 600 Hz bin separation, and a 32-channel array, as a non-limiting example. FIG. 4 illustrates phantom images including the ideal sum of squares combined image (A), calibration combined image (B), aliased and un-aliased half field of view images (C and D, respectively), aliased and un-aliased quarter field of view images (E and F, respectively), and aliased and un-aliased eighth field of view images (G and H, respectively).

Figure 5:
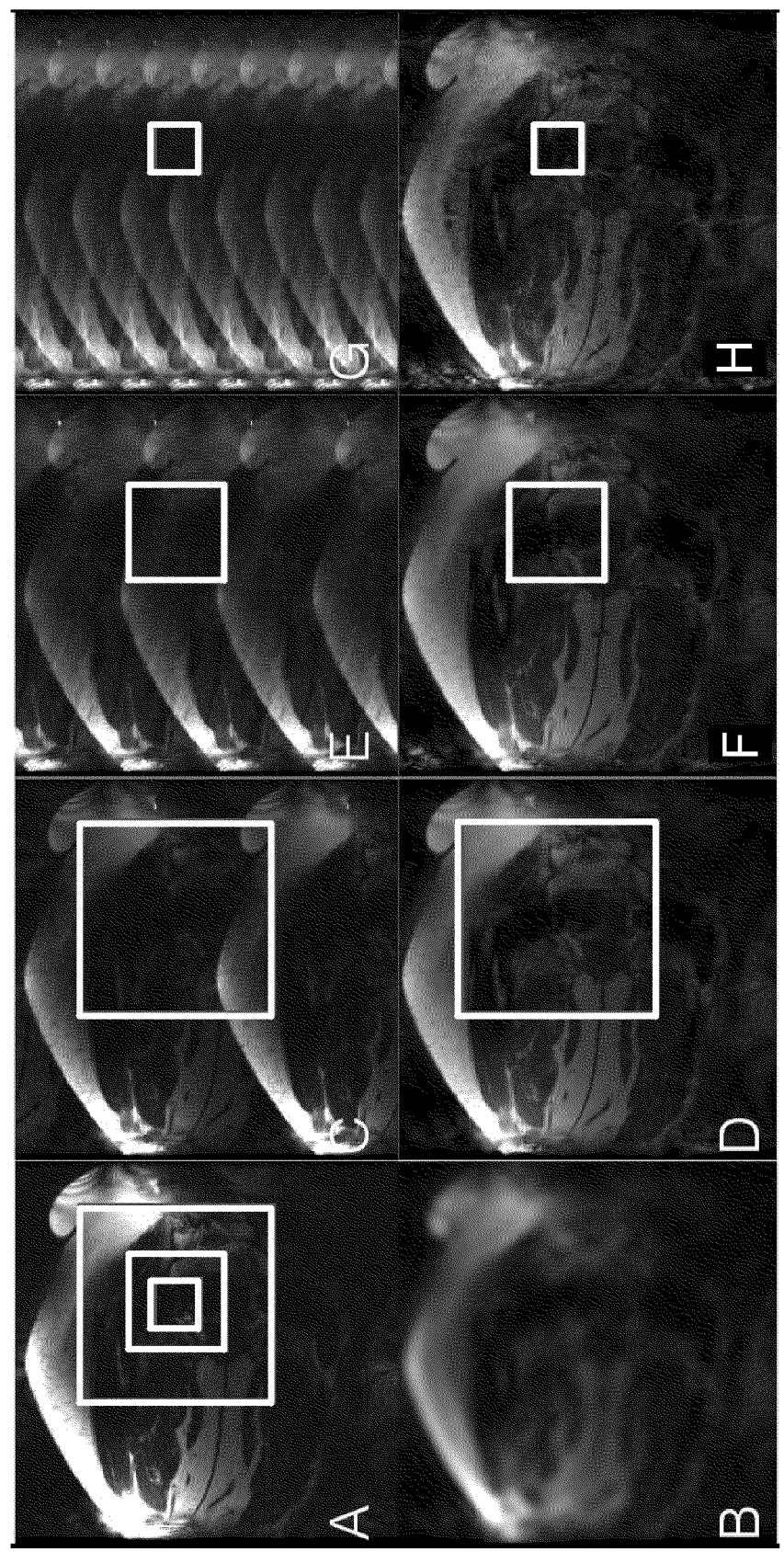
FIG. 5 shows experimental results based on two dimensional MSI acquisition on a patient with bilateral hip replacements.

FIG. 5 shows experimental results based on two dimensional MSI acquisition on a patient with bilateral hip replacements (imaged using GE Discovery MR450 1.5T). The imaging parameters were identical matching parameters (as those described with respect to FIG. 4), except 24 frequency bins were employed. FIG. 5 includes the ideal sum of squares combined image (A), calibration combined image (B), aliased and un-aliased half field of view images (C and D, respectively), aliased and un-aliased quarter field of view images (E and F, respectively), and aliased and un-aliased eighth field of view images (G and H, respectively).

For both FIGS. 4 and 5, data were retrospectively decimated to obtain reduction factors of 2, 4, and 8 in the phase encoding direction to simulate half, quarter, and one eighth field of views, for example. For calibration (or pre-scan), the central 32×32 matrix of k-space was extracted from each coil and each bin before decimation. Alternatively, a separate low-resolution calibration acquisition can be used in place of this method. A standard SENSE algorithm was applied in which each coil sensitivity signal was replaced by a coil-bin combination. Thus, in the phantom case with a 32-channel coil and 16 bins, "sensitivity encoding" was effectively achieved with 512 elements.

Figure 6:
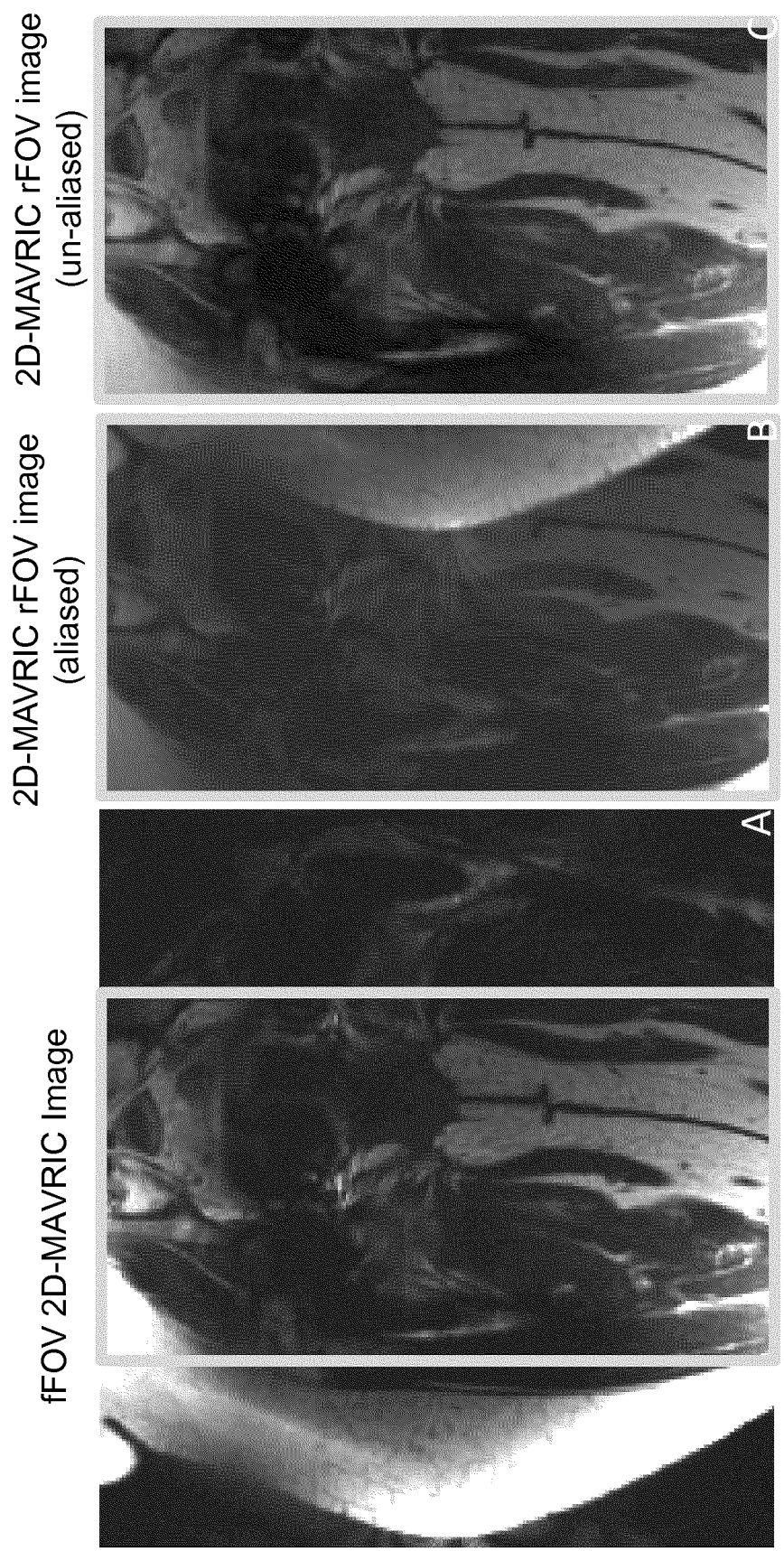
FIG. 6 shows experimental results illustrating final half field of view images for the patient data of FIG. 5 before and after un-aliasing.

FIG. 6 shows experimental results illustrating final half field of view images for the patient data of FIG. 5 before and after un-aliasing. FIG. 6 includes a fFOV image (A), half FOV image before aliasing (B), and half FOV image after aliasing (B).

It is clear that images were reconstructed with an effective reduction factor of 4 with minimal residual aliasing artifact, even outside of the reduced field of view. It is noted that the reduced field of view neighborhood of the implant can be effectively reconstructed without artifact with even higher reduction factors because of the smaller spatial extent of the "sensitivity profiles" from the frequency bins in that area. This is particularly evident in the case of the 8× field of view reduction with the phantom. The small spatial extent of those bins greatly reduces the available signal to alias with the reduced field of view arising from the sub-sampled k-space.

It should be noted that the images shown in FIGS. 4-6 utilized 2D-MSI technology, whereby MSI spectral bins are defined by modulating excitation, refocusing, and signal reception frequencies in a spin-echo based pulse sequence that inverts the polarity of the excitation and refocusing slice-selection gradients. All of the presented embodiments are also compatible with 3D-MSI (e.g., MAVRIC, SEMAC, MAVRIC SL).

It should be noted that certain passages of this disclosure can reference terms such as "first" and "second" in connection with scans, fields of view, etc., for purposes of identifying or differentiating one from another or from others. These terms are not intended to merely relate entities (e.g., a first field of view and a second field of view) temporally or according to a sequence, although in some cases, these entities can include such a relationship. Nor do these terms limit the number of possible entities (e.g., devices) that can operate within a system or environment.

It should be understood that the systems described above can provide multiple ones of any or each of those components and these components can be provided on either a standalone machine or, in some embodiments, on multiple machines in a distributed system. In addition, the systems and methods described above can be provided as one or more computer-readable programs or executable instructions embodied on or in one or more articles of manufacture. The article of manufacture can be a floppy disk, a hard disk, a CD-ROM, a flash memory card, a PROM, a RAM, a ROM, or a magnetic tape. In general, the computer-readable programs can be implemented in any programming language, such as LISP, PERL, C, C++, C#, PROLOG, or in any byte code language such as JAVA. The software programs or executable instructions can be stored on or in one or more articles of manufacture as object code.

While the foregoing written description of the methods and systems enables one of ordinary skill to make and use various embodiments of these methods and systems, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

What is claimed is:

1. A magnetic resonance imaging (MRI) system comprising:
   a MRI scanner, including a plurality of radio frequency (RF) receivers, for imaging objects of interest;
   at least one processor; and
   a memory, with computer code instructions stored thereon, the computer code instructions, when executed by the at least one processor, cause the at least one processor to:
   cause the MRI scanner to perform a first scan, on an anatomy region including an implant, according to a first field of view to acquire first multi-spectral MRI data associated with a plurality of frequency bins;
   compute, for each pair of a single RF receiver and a single frequency bin, a respective spectral sensitivity map using at least a portion of the first multi-spectral MRI data;
   cause the MRI scanner to perform a second scan according to a second field of view to acquire second multi-spectral MRI data associated with the plurality of frequency bins, the second field of view smaller than the first field of view; and
   reconstruct one or more MRI images according to the second field of view using the second multi-spectral MRI data and the spectral sensitivity maps.

2. The magnetic resonance imaging (MRI) system of claim 1, wherein the first field of view is a full field of view.

3. The magnetic resonance imaging (MRI) system of claim 1, wherein reconstructing the one or more MRI images according to the second field of view includes applying autocalibrated parallel imaging to the second multi-spectral MRI data prior to performing unaliasing of the second multi-spectral MRI data.

4. The magnetic resonance imaging (MRI) system of claim 1, wherein performing the second scan includes selecting a "no phase-wrap" option or a "fold-over suppression" option when acquiring second multi-spectral MRI data, selection of the "no phase-wrap" option or the "fold-over suppression" option causing the processor to perform unaliasing on the second multi-spectral MRI data using the sensitivity maps.

5. The magnetic resonance imaging (MRI) system of claim 1, wherein the first field of view is an integer multiple of the second field of view.

6. The magnetic resonance imaging (MRI) system of claim 1, wherein the first field of view is a non-integer multiple of the second field of view.

7. The magnetic resonance imaging (MRI) system of claim 1, wherein reconstructing the one or more MRI images according to the second field of view includes performing unaliasing correction to the to the second multi-spectral MRI data in image-space (x,y,z).

8. The magnetic resonance imaging (MRI) system of claim 1, wherein reconstructing the one or more MRI images according to the second field of view includes performing unaliasing correction to the second multi-spectral MRI data in k-space (kx,ky,kz).

9. The magnetic resonance imaging (MRI) system of claim 1, wherein reconstructing the one or more MRI images according to the second field of view includes performing unaliasing correction to the second multi-spectral MRI data in a hybrid space, the hybrid space including one or more dimensions in image-space and one or more dimensions in k-space.

10. A magnetic resonance imaging (MRI) method comprising:
   performing, by a MRI scanner having a plurality of radio frequency (RF) receivers, a first scan according to a first field of view to acquire first multi-spectral MRI data associated with a plurality of frequency bins and corresponding to an anatomy area including an implant;
   generating, by a processor for each pair of a single RF receiver and a single frequency bin, a respective spectral sensitivity map using at least a portion of the first multi-spectral MRI data;
   performing, by the MRI scanner, a second scan according to a second field of view to acquire second multi-spectral MRI data associated with the plurality of frequency bins and corresponding to the anatomy area including an implant, the second field of view smaller than the first field of view; and
   reconstructing, by the processor, one or more MRI images according to the second field of view using the second multi-spectral MRI data and the spectral sensitivity maps.

11. The magnetic resonance imaging (MRI) method of claim 10, wherein the first field of view is a full field of view.

12. The magnetic resonance imaging (MRI) method of claim 10, wherein reconstructing the one or more MRI images according to the second field of view includes applying autocalibrated parallel imaging to the second multi-spectral MRI data prior to performing unaliasing of the second multi-spectral MRI data.

13. The magnetic resonance imaging (MRI) method of claim 10, wherein performing the second scan includes selecting a "no phase-wrap" option or a "fold-over suppression" option when acquiring the second multi-spectral MRI data, selection of the "no phase-wrap" option or the "fold-over suppression" option causing the processor to perform unaliasing on the second multi-spectral MRI data using the sensitivity maps.

14. The magnetic resonance imaging (MRI) method of claim 10, wherein the first field of view is an integer multiple of the second field of view.

15. The magnetic resonance imaging (MRI) method of claim 10, wherein the first field of view is a non-integer multiple of the second field of view.

16. The magnetic resonance imaging (MRI) method of claim 10, wherein reconstructing the one or more MRI images according to the second field of view includes performing unaliasing correction to the to the second multi-spectral MRI data in image-space (x,y,z).

17. The magnetic resonance imaging (MRI) method of claim 10, wherein reconstructing the one or more MRI images according to the second field of view includes performing unaliasing correction to the second multi-spectral MRI data in k-space (kx,ky,kz).

18. The magnetic resonance imaging (MRI) method of claim 10, wherein reconstructing the one or more MRI images according to the second field of view includes performing unaliasing correction to the second multi-spectral MRI data in a hybrid space, the hybrid space including one or more dimensions in image-space and one or more dimensions in k-space.

19. A non-transitory computer-readable medium comprising computer executable instructions stored thereon, the computer executable instructions when executed by a processor, cause the processor to:
   cause the MRI scanner to a perform a first scan according to a first field of view to acquire first multi-spectral MRI data associated with a plurality of frequency bins and corresponding to an anatomy area including an implant;
   generate, for each pair of a single RF receiver and a single frequency bin, a respective spectral sensitivity map using at least a portion of the first multi-spectral MRI data;
   cause the MRI scanner to a perform a second scan according to a second field of view to acquire second multi-spectral MRI data associated with the plurality of frequency bins and corresponding to the anatomy area including an implant, the second field of view smaller than the first field of view; and
   reconstruct one or more MRI images according to the second field of view using the second multi-spectral MRI data and the spectral sensitivity map.

20. The non-transitory computer-readable medium of claim 19, wherein the first field of view is a full field of view.

* * * * *